United States Patent [19]

Waterman et al.

[11] Patent Number: 5,064,429
[45] Date of Patent: Nov. 12, 1991

[54] SKIN GATHERING AND HOLDING DEVICE

[75] Inventors: Glenn N. Waterman, Holladay; Fredrick A. Gibbs, Salt Lake City, both of Utah

[73] Assignee: Diacor, Inc., Salt Lake City, Utah

[21] Appl. No.: 615,566

[22] Filed: Nov. 19, 1990

[51] Int. Cl.$^5$ .............................................. A61B 17/00
[52] U.S. Cl. .................................................. 606/151
[58] Field of Search ............... 606/158, 151, 157, 131, 606/205-208; 128/677-679, 888, 899, 846; 227/901

[56] References Cited

U.S. PATENT DOCUMENTS

| | | | |
|---|---|---|---|
| 2,491,050 | 12/1949 | McAdoo | 606/151 |
| 3,598,125 | 8/1971 | Cogley | 606/157 |
| 4,269,190 | 5/1981 | Behney | 606/157 |
| 4,822,348 | 4/1989 | Casey | 606/157 |
| 4,931,058 | 6/1990 | Cooper | 606/158 |
| 4,943,298 | 7/1990 | Fujita et al. | 606/151 |
| 5,009,654 | 4/1991 | Minshall et al. | 604/408 |

FOREIGN PATENT DOCUMENTS 3600789 7/1987 Fed. Rep. of Germany ...... 606/151

OTHER PUBLICATIONS

Undated Baxter Edwards Advertising Literature.

Primary Examiner—Stephen C. Pellegrino
Assistant Examiner—Gary Jackson
Attorney, Agent, or Firm—Lynn G. Foster

[57] ABSTRACT

Loose skin grasping and holding devices for use in transdermal radiation medical therapy whereby the loose skin and related tissue are held safely away from the treatment area during radiation. The devices comprise clamping mechanism which connect to radiologically transparent dermal grasping pads which close upon and hold the loose skin away from the treatment site. One of the disclosed devices comprises a compressive spring memory mechanism by which the opposed pads are normally biased toward each other. The second disclosed device comprises a latching connection similar in action to forceps. The pads comprise high density synthetic resinous foam, such as styrofoam, which is or may be contoured to safely and adequately engage the skin.

22 Claims, 3 Drawing Sheets

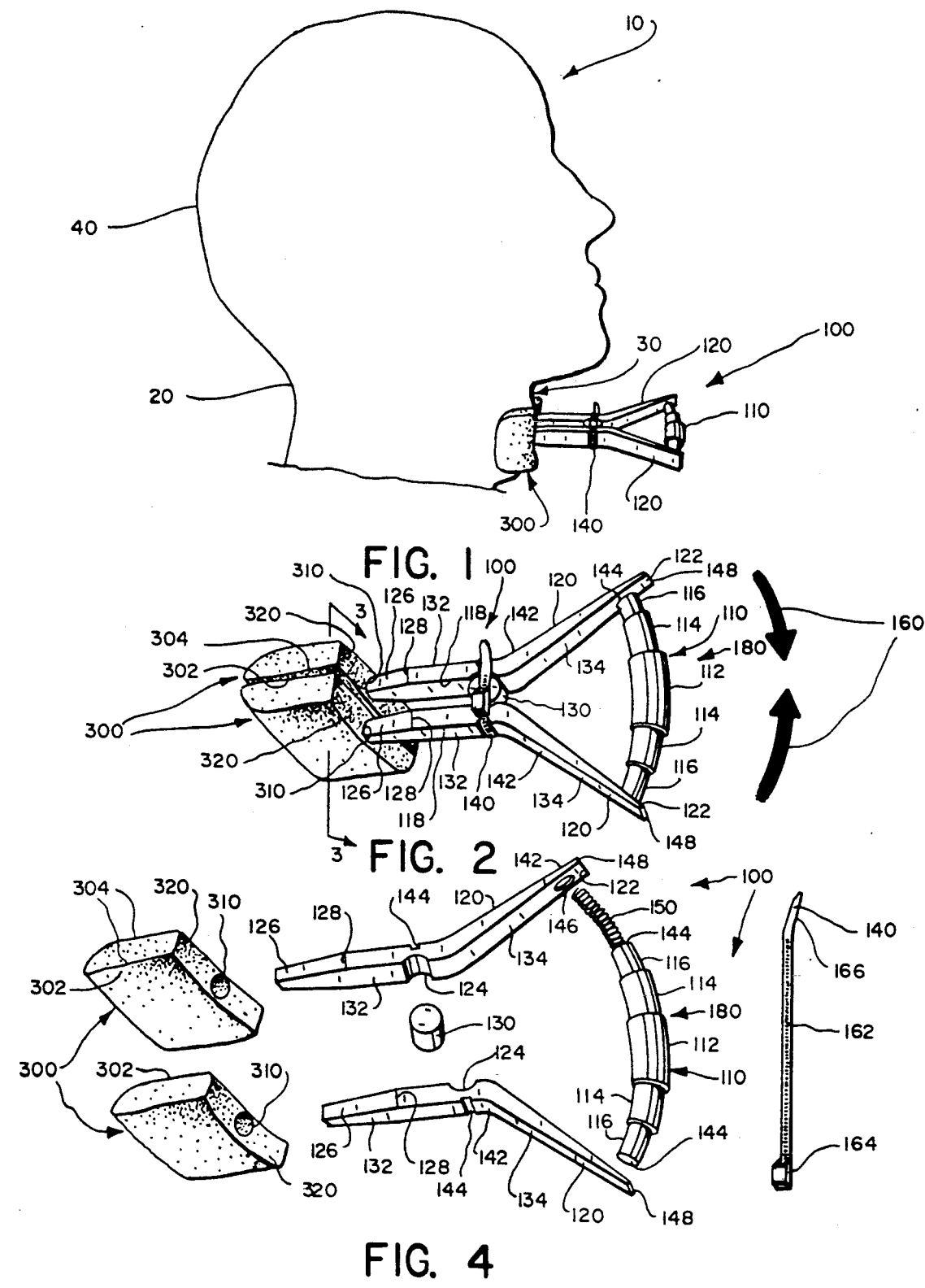

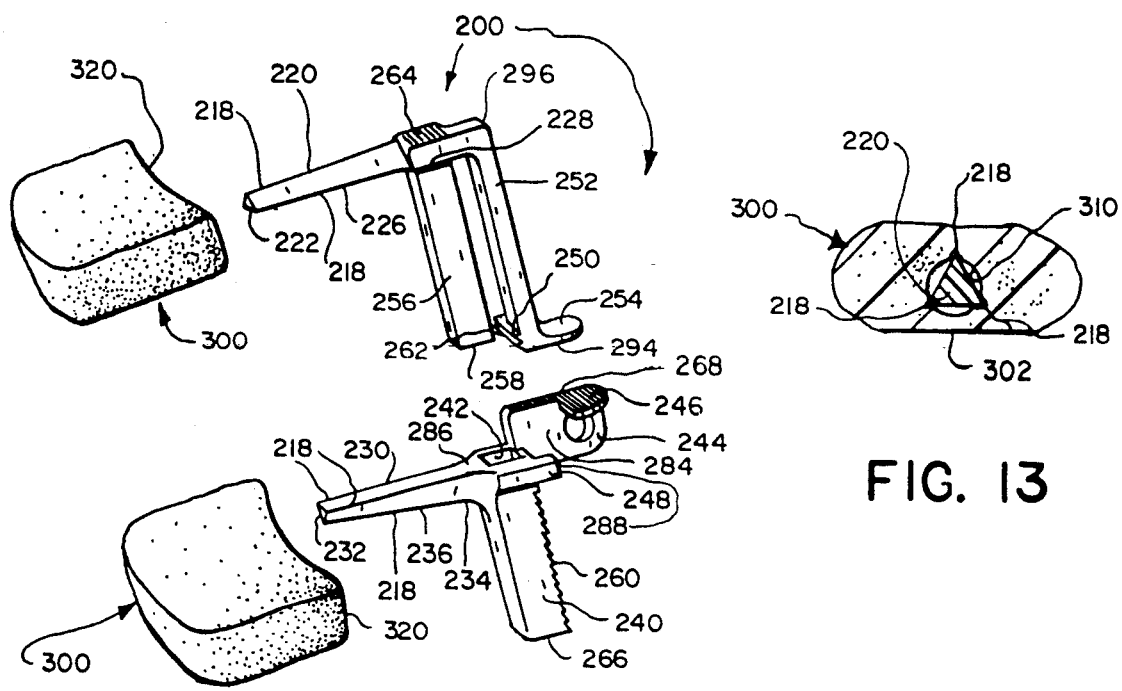
FIG. 11
FIG. 13
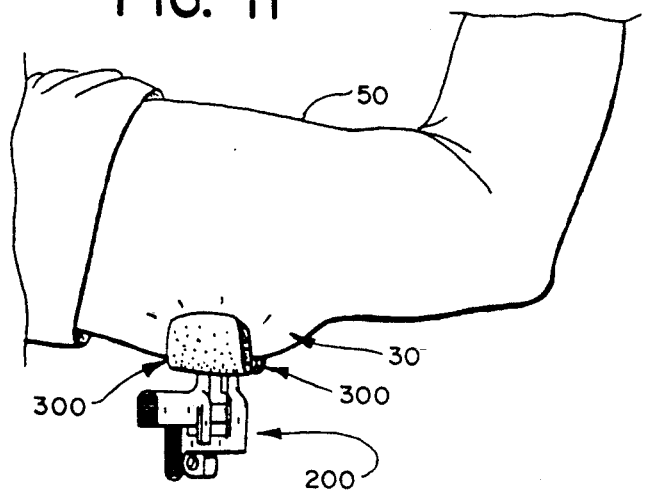
FIG. 9
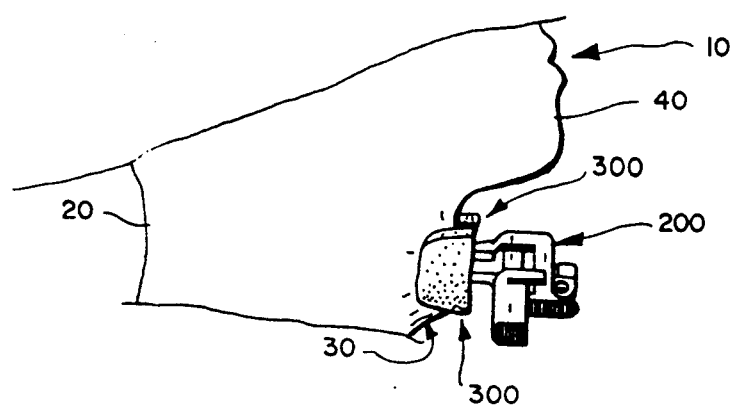
FIG. 8

SKIN GATHERING AND HOLDING DEVICE

FIELD OF INVENTION

This invention relates to devices used in medical procedures and more particularly to a clamp device which releasibly gathers and holds skin, typically as folds, counter to the normal position thereof, for safety and protection of patient tissues during therapy.

RELATED ART

During radiation therapy upon patient extremities comprising arms, legs, and the head and neck, especially during multiple high dose treatments wherefrom a cure is sought, it is highly desirable to move and retain excess skin from the target area. Such therapy is commonly used to combat extremity tumors and six or more treatments may be required to achieve a cure.

Protecting the target areas from radiation damage has been a longstanding problem. Radiation injury to loose and bulky layers of skin and related tissue at the target area has frequently occurred. Such damage to the dermal and epidermal skin layers and to lymphatic drainage systems detour rapid recovery and sometimes are permanent.

BRIEF SUMMARY AND OBJECTS OF THE INVENTION

In brief summary, this novel invention alleviates known problems related to removing and releasibly holding portions of skin from a target segment of a patient during radiation therapy and the like. The device comprises skin-contacting and grasping clamping pads, each of which may be sterilized. The clamping pads are biased into the clamping position by a spring-loaded pincher or a self-locking, releasible clamp which may be similar to the action of forceps. The skin-contacting pads hold excess skin away from the target area while placing the skin remaining at the target area in taut condition. Radiation as used herein refers to therapeutic radiation used in medical practice to treat and cure diseases comprising cancer, tumors and the like.

The skin-contacting pads are preferably essentially transparent to radiation and radiation scatter free, even though the pads are desirably removed from the radiation path. The skin-contacting pad material comprises opposed clamping surfaces which retain skin therebetween and outside the target area while spreading the clamping forces over a relatively large contact area of the skin so there is little if any patient discomfort. The skin-contacting pads may be selectively removable from the clamping portion such that the skin-contacting pads are removable and exchangeable and the clamping portion is reusable. Nevertheless, if desired, the entire apparatus may be disposable.

With the foregoing in mind, it is a paramount object of the present invention to provide a novel device, and related methods, by which problems of the past are overcome or substantially alleviated.

It is a primary object to provide a device which holds skin folds and associated parts displaced from potentially damaging radiation during radiation treatment for cancer and the like.

It is a main object to provide a skin fold holding device which comprises a clamping portion and skin-contacting pads.

It is a principal object to provide a skin holding device comprising a clamping portion which gently biases skin-contacting pads whereby loose skin captured between the skin-contacting pads is releasibly constrained away from a target area for radiation therapy.

It is a chief object to provide novel skin-contacting pads which clamp against and restrain skin in a desired position.

It is a further principal object to provide a skin grasping device for use in radiation therapy which comprises a clamp and opposed, large area skin-contacting pads which are bias toward each other by the clamp.

It is an important object to provide skin-contacting pads carried by a clamp wherein the pads are essentially transparent to radiation.

It is another significant object to provide a novel device for releasibly holding excess skin away from a target site for radiation therapy and the skin at the site taut, without inducing patient pain or trauma.

Another important object of the present invention is provision of a skin holding clamp comprising pads of foamed synthetic resinous material.

These and other objects and features of the present invention will be apparent from the detailed description taken with reference to accompanying drawings.

BRIEF DESCRIPTION OF THE DRAWINGS

FIG. 1 is a side perspective of a skin displacement device affixed to and pulling a fold of neck skin away from normal state and position;

FIG. 2 is a perspective of the skin displacement device seen in FIG. 1;

FIG. 4 is an exploded view of the skin displacement device of FIG. 2;

FIG. 8 is a side fragmentary view of a patient and a skin displacement device affixed to a skin fold on the neck of a patient;

FIG. 9 is a fragmentary side perspective of the skin displacement device of FIG. 8 affixed to a skin fold on the limb of a patient;

FIG. 11 is an exploded perspective of the skin displacement device of FIG. 10 with skin-contacting pads;

FIG. 13 is a full cross sectional view along lines 13—13 of FIG. 12 showing the compressive connection of the corners of an inserted member into a skin-connection pad.

DETAILED DESCRIPTION OF THE ILLUSTRATED EMBODIMENTS

Figures 3, 5:
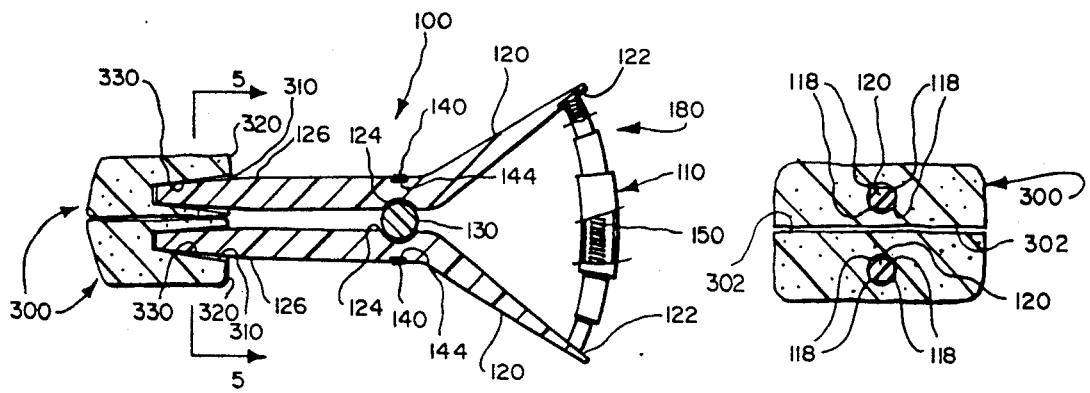
FIG. 3 is a cross sectional view along lines 3—3 of FIG. 2 showing segments broken away for clarity.
FIG. 5 is a full cross sectional view along lines 5—5 of FIG. 3.

In this description, the term proximal is used to indicate the segment of the device normally closest to an operator or technician who is applying the device to the patient. The term distal refers to the other end. Reference is now made to the embodiments illustrated in FIGS. 1-13 wherein like numerals are used to designate like parts throughout. All parts are, unless otherwise designated, made of synthetic resinous material which is transparent to radiation, neither absorbing nor scattering radiation traveling therethrough.

A currently preferred embodiment of the invention is seen in FIG. 1 wherein a skin displacement device 100 is seen coupled through skin-contacting pads 300 to the neck 20 of a patient 10 thereby holding a fold of skin 30 protracted away from areas where it is normally disposed below the head 40 of patient 10. Such skin displacement removes looser skin from treatment target areas, provides a smaller skin target area for a beam of radiation or the like, and thereby preserves large segments of the skin of patient 10 and associated lymph drainage systems for the subsequent healing process.

As seen in FIG. 2 and in more detail in FIGS. 3-4, skin displacement device 100 comprises two lever members 120, a spring mechanism 180, a uniting band 140, and a fulcrum 130. Skin-contacting pads 300, shown in FIGS. 2-4, are discussed separately hereafter. Each lever member 120 comprises a distal segment 132 and a proximal segment 134. Separation between segments 132 and 134 is marked by arcuate groove 124 which is part of internal surface 122 of each lever member 120 and wherein fulcrum 130 is located when the two lever members 120 are united in mirror image orientation and fastened together by band 140 thereby containing fulcrum 130 therein. A second rectangular groove 144 on outside surface 142 provides a positioning and locking slot for uniting band 140.

Distal end 132 comprises a nearly square distally linearly shrinking cross section which comprises a pyramiding shaped end 126, distal to line 128, to which a skin-contacting pad is compressibly, firmly, but releasibly, affixed as explained hereafter. At the proximal edge of groove 124, proximal segment 134 angles obliquely away from groove 124 side of distal segment 132, as best seen in FIG. 4. Near proximal end 148, proximal segment 134 comprises circular depression 146 countersunk into surface 122 for reasons which are explained hereafter.

Fulcrum 130, which provides a leveraged connection between two facing lever members 120, comprises a cylindrical shape which fits into each oppositely facing groove 124. Uniting band 140 comprises a self locking strap made of pliable synthetic resinous material and similar in construction and material to an electronic cable tie. Uniting band 140 comprises raised teeth 162 along one surface and a receiving lockbuckle 164 on a receiving end which receives insertion end 166 of uniting band 140 in one direction, but permanently retards removal in the other direction. Once inserted and pulled in tight relation, uniting band 140 provides a hingeable girdle within which lever members 120 ride on fulcrum 130 to selectively open and close alternate ends of the facing lever members 120 of skin displacement device 100.

When assembled, a restraining force for skin displacement device 100 is provided by spring mechanism 180. Spring mechanism 180 comprises a telescopic housing 110 which covers a compression spring 150. Although different spring housings are usable within the scope of the invention, hollow telescoping housing 110 comprising a central housing member symmetrically disposed about the longitudinal central axis of skin displacement device 100 and telescopically attached on each end to a medial housing member 114 which is further telescopically attached to lateral housing member 116 comprises the housing for compression spring 150 in this embodiment. Each free end 144 of each lateral housing member 116 fits snugly into depression 144 of each lever member 120 and is therein retained when skin displacement device 100 is assembled and held together by band 140. Compression spring 150 comprises a length which is substantially larger than the arc length of hollow telescopic housing 110 such that compressive force is provided in the non-skin-fold-seizing state. When skin displacement device 100 is disposed in skin fold 30 seizing position, compression spring 150 comprises compressive spring force sufficient to retain a skin fold 30 firmly yet without injury inside skin-contacting pads 300. Such force is consistent with the force exerted upon closing members of a clothes pin. Since compression spring 150 may be metallic and, therefore, not acceptably transparent to radiation, it is important that compression spring 150 be located remotely from the patient 10 target site and, therefore, from the skin-contacting pads. Thus, telescopic housing 110 is disposed proximal to the operator and removed distally from skin fold 30.

Assembly of skin displacement device 100 comprises placing two lever members 120 with like interior surface juxtaposed, inserting compression spring 150 into the central tubular cavity of hollow telescopic housing 110 and further inserting each free end 146 of each lateral housing member 116 into each depression 144. Fulcrum 130 is inserted between juxtaposed grooves 124 and uniting band 140 is wrapped around both lever members 120 at grooves 144 and, thereby, capturing fulcrum 130. End 166 is inserted into lock buckle 164 and pulled tight to form an apparatus which responsively separates distal members 132 when proximal segments 134 are squeezed together in the direction shown by arrows 160 in FIG. 1, but compressively returns and forces distal members 132 one toward the other when the squeezing force is released.

Figures 6, 7:
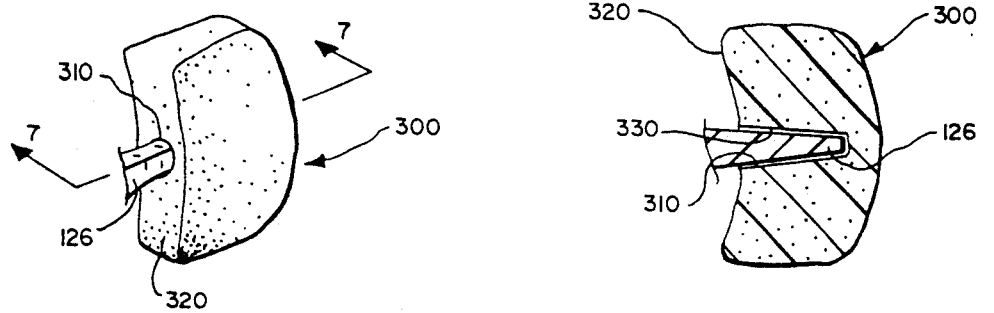
FIG. 6 is a perspective of a skin-contacting pad seen first on the neck of the patient in FIG. 1.
FIG. 7 is a cross section along lines 7—7 in FIG. 6.

Reference is now made to FIGS. 2-7, wherein the interface between the skin displacement device 100 and each skin-contacting pad 300 is seen. One skin-contacting pad 300 is seen attached to the pyramidally-shaped end 126 of each lever member 120 of assembled skin displacement device 100 in FIG. 2 and seen similarly, but fragmentarily in FIG. 6. Each skin-contacting pad 300 comprises a paddle shape comprising at least one flat side 302, a proximal surface 320 and a thickness which allows insertive attachment by a lever member 120. See FIG. 5. The external corners 304 are rounded or softened to prevent injury to the skin of a patient 10. As best seen in FIGS. 4 and 6, proximal surface 320 comprises a centrally disposed orifice 310 where a frustoconical aperture 330 inwardly extends. The apical angle of frustoconical aperture 330 is substantially the same as the angle of expansion of the pyramidally-shaped end 126 of each lever member 120. See FIG. 7. The surface area of each surface 302 is sufficiently broad to grasp a skinfold of a patient and skin-contacting pads 300 are made in varying sized parts for different patient sizes and positions of application. Each skin-contacting pad 300 is preferably made of high-density foamed synthetic resinous material. As an example, DOW Chemical Company XUS 44000.1 (or equivalent) may be used for skin-contacting pad manufacture. By using foamed synthetic resinous material, the manufacturer and/or user can shape the pads as desired using a cutting instrument, sand paper and/or the like. Such skin-contacting pads are preferably sterilized prior to use, using standard gas or radiation sterilization methods and equipment.

A releasable connection, resulting in a firm attachment, of each lever member 120 to a skin-contacting pad 300 is accomplished by inserting lever member 120 into frustoconical aperture 330 until the corners 118 of lever member 120 bite into the surface of surrounding aperture 330, much as a hand tool, such as a screw driver or the like, is fitted with a wooden handle. As seen in FIGS. 3, 5, and 7, other than at the corners there is little or no contact between the surfaces of lever member 120 and skin-contacting pad 300. However, as best seen in FIG. 5, corners 118 compressively deform contacting segments of aperture 330 as distal segment 126 is tightly inserted, providing an attachment which resists removal and rotation when in use. After use, each used skin-contacting pad 300 is pulled linearly away from distal segment 126 for removal and disposal.

In use, a skin-contacting pad 300 is attached to each lever member 120. Both skin-contacting pads 300 and skin displacement device 100 may be sterilized before use by gas or radiation sterilization equipment and processes which are available in the art. An extended skin fold 30 is provided by a technician or an operator by grasping a fold of skin between the digital extremities of the hand and pulling the fold 30 proximally. The skin-contacting pads 300 are separated by squeezing the lever members 120 together as shown by arrows 160. The, thus separated skin-contacting pads 300, are placed in contact with the fold 30 and the squeezed lever members 120 are released to provide full compressive and retaining pressure on the skin-contacting pads 300 and skin fold 30. After completion of a treatment the skin displacement device 100 is removed by once again squeezing the lever members 120 together freeing the skin fold 30 to return to a predisposed position and state.

Figures 10, 12:
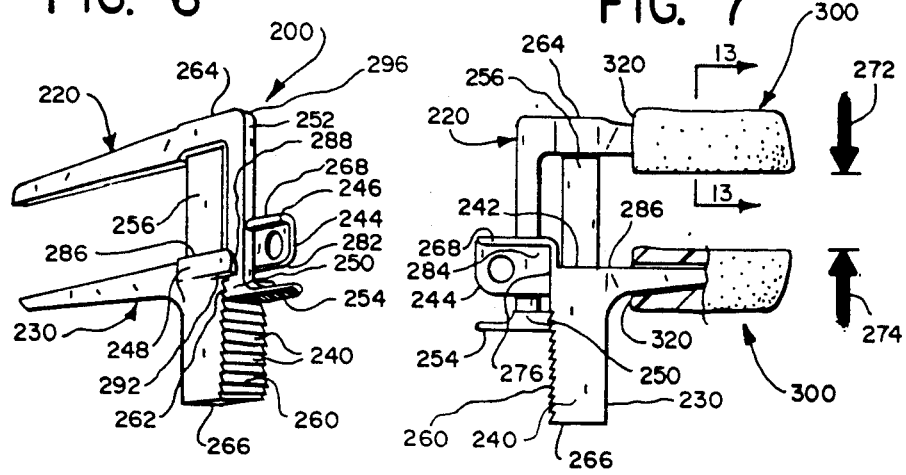
FIG. 10 is a perspective of the skin displacement device of FIG. 8, without skin-contacting pads.
FIG. 12 is a side view of the skin displacement device of FIG. 11, assembled with skin-contacting pads with a portion of one skin-contacting pad removed for clarity.

Another currently preferred skin displacement device 200 is seen in FIG. 10. Skin displacement device 200 comprises two joinable parts, captive part 220 and capture part 230, each of which interface and releasibly connect to a skin-contacting pad 300 in similar manner to the connection made by lever members 120, earlier described. Rather than pressure being provided by a compressive spring 150 as described for skin displacement device 100, skin displacement device 200 comprises a releasible locking, forceps like, action whereby force to a skin fold 30 is directly applied by an operator's or technician's squeeze. As seen in FIG. 10, displacement device 200 is similar in shape and operation to a disposable forceps manufactured and distributed by Baxter Edwards, P.O. Box 11150, Irvine, Cal., 92714, called the Edwards Single Softjaw and Double Softjaw Handless Clamps.

Each part of displacement device 200 is seen separately in FIG. 11. Capture part 230 comprises three major members, ratchet bar 240, side guide and interlock 244, and skin-contacting pad connecting bar 236. Ratchet bar 240 is the main or supporting stem for capture part 230 and comprises a side comprising ratchet teeth 260, a rectangular guide channel 242, a capture guide 248, and joining interface 234, to skin-contacting pad connecting bar 236, and joining interface 276 (see FIG. 12), to side guide and interlock 244. Rectangular guide channel 242, axially and longitudinally disposed through the length of ratchet bar 240, is open at a top side 286 to receive a guide bar 256 of captive part 220 and closed on a bottom side 266 whereat a tread is provided for easier handling. On a side adjacent the side comprising ratchet teeth 260 and near top side 286, ratchet bar 240 is broadened laterally to comprise capture guide 248. Capture guide 248 comprises an extending part 288 which extends laterally from ratchet bar 240 orthogonal to the plane of the side comprising ratchet teeth 260 to provide a guide for a release bar 252 of captive part 220.

Joining interface 234 provides contiguous extension of ratchet bar 240 along top side 286 to form skin-contacting pad connection bar 236 on the side opposite the side comprising ratchet teeth 260. See FIG. 11. Skin-contacting pad connection bar 236 comprises a long nosed connector, which is triangular in cross section with one side in the plane of top side 286. The cross section of skin-contacting pad connection bar 236 linearly diminishes with outward extension from ratchet bar 240 to an end 232. Connection of a skin-contacting pad 300 to skin-contacting pad connection bar 236 is similar to the earlier described connection between a skin-contacting pad 300 and lever member 120 except that skin-contacting pad connection bar 236 comprises three connecting corners rather than four. As seen in FIG. 13, insertion of skin-contacting pad connection bar 236 into a skin-contacting pad 300, compressibly deforms the surface of aperture 310 at each interfacing corner 218, making a firm and stable but removable connection.

As seen in FIG. 12, on the side opposite capture guide 248, joining interface 276 contiguously connects ratchet bar 240 to side guide and interlock 244. Side guide and interlock 244 comprises a plate 284 extending orthogonal to and outward from the face of the side comprising ratchet teeth 260. As best seen in FIG. 11, plate 284 also extends upward above top side 286 terminating along top tread line 268 whereat a tab 246 is formed. As best seen in FIG. 10, tab 268 is formed as an orthogonally attached plate to the top of side guide and interlock 244. The side of tab 268 proximal to the plane of the side comprising ratchet teeth 260 is displaced away from said plane a distance which allows a release bar 252 to easily slide along said plane, while acting as a guide for release bar 252. The bottom 282 of side guide and interlock 244 is juxtaposed with the bottom 292 of capture guide 248 and provides a stop, limiting separating travel between capture part 230 and captive part 220, as will be described in more detail later.

As best seen in FIG. 11, captive part 220 comprises skin-contacting pad connection bar 226, guide bar 256, and ratchet release bar 252. Guide bar 256 comprises a rectangular bar which fits into and smoothly slides along rectangular guide channel 242. A cross member 228 forms a "T" connection among the downwardly distending guide bar 256 and adjoining ratchet release bar 252 and skin-contacting pad connection bar 226. Skin-contacting pad connection bar 226, comprising end 222, is similar in form and function to skin-contacting pad connection bar 236 but of mirror image orientation. Along the top of cross member 228, directly above guide bar 256, a pad 264 comprising tread markings provides a place for a finger or the like where compressive force is applied as explained in detail later.

In opposite relation to the extension of skin-contacting pad connection bar 226, cross member 228 extends laterally, then orthogonally turns downward at corner 296 to form ratchet release bar 252. Ratchet release bar 252 comprises teeth 262 and is offset from guide bar 256 a distance, such that, when guide bar 256 is inserted into rectangular guide channel 242 ratchet release bar 252 comprises a pawl 250 for ratchet teeth 260. Further at the bottom 294 of ratchet release bar 252 an orthogonal foot 254 comprising a lateral extension which extends below side guide and interlock 244 to provide a travel limiting interlock preventing inadvertent separation when captive part 220 is operably joined with capture part 230. Tread-like markings are placed on the bottom of orthogonal foot 254 to improve handling.

Skin displacement device 200 is assembled by inserting the bottom 258 of guide bar 256 into rectangular channel 242 and snapping ratchet release bar 252 into guided and interlocked disposition among capture guide 248, side guide and interlock 244, and tab 268. In use, one skin-contacting pad 300 is attached to each skin-contacting pad connection bar 226 and 236, respectively.

To apply skin-fold displacement device 200, an extended skin fold 30 is acquired by a technician or an operator by grasping a fold of skin between the digital extremities of a hand and pulling the fold 30 proximally. The skin-contacting pads 300 are separated by sliding captive part 220 and capture part 230 apart until orthogonal foot 254 is limited from further travel by contact with bottom 282 of side guide and interlock 244. The, thus separated skin-contacting pads 300, are placed about fold 30 and pressure is applied to pad 264 and bottom side 266 to apply compressive and retaining pressure, in direction of arrows 272 and 274, on the skin-contacting pads 300, as seen in FIG. 12. The skin-fold is captured thereby as seen in FIGS. 8 and 9. After completion of therapy, the skin displacement device 100 is removed by applying a forefinger or the like against tab 246 while urging the bottom 254 of ratchet release bar 252 outwardly, as shown by arrow 270 in FIG. 12, to release pawl 250 from contact, thereby releasing captive part 220, and sliding skin-contacting pad connecting bars 226 and 236 apart and, thereby, separating opposing skin-contacting pads 300 and freeing skin fold 30 to return to a predisposed position and state.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. Skin clamping structure for releasibly holding skin away from a treatment site during medical therapy, said clamping structure comprising:
    radiation-transparent dermal grasping means comprising opposed surface means each of substantial area which contiguously engage skin and attachment means;
    clamping means comprising connection means by which the clamping means are connected to the attachment means, bias means, bifurcated bias applying means by which the opposed surface means are caused to be biased toward each other and manual actuation means by which the bias applying means are selectively displaced counter to the bias to open the opposed surface means.

2. Structure according to claim 1 wherein said clamping means comprise forceps means.

3. Structure according to claim 2 wherein said forceps means comprise disposable forceps means comprising synthetic resinous material.

4. The skin clamping structure for releasibly holding skin away from a treatment site during medical therapy, said clamping structure comprising:
    radiation-transparent dermal grasping means comprising opposed surface means each of substantial area which contiguously engage skin and attachment means;
    clamping means comprising connection means by which the clamping means are connected to the attachment means, bias means, bifurcated bias applying means by which the opposed surface means are caused to be biased toward each other and manual actuation means by which the bias applying means are selectively displaced counter to the bias to open the opposed surface means;
    the clamping means comprise radiation transparent material.

5. The structure according to claim 4 wherein the grasping means comprise single use, disposable means and the clamping means comprise multiple use means, said connection between the connection means and the attachment means is manually separable to accommodate discarding of the grasping means after a single use.

6. The structure according to claim 4 wherein said grasping means are configured and contoured to prevent or alleviate injury.

7. The structure according to claim 4 wherein said attachment means comprise frustoconical cavity means and said connection means comprise male insertion means sized and shaped to be received on an interference basis in the cavity means.

8. Structure according to claim 7 wherein the male insertion means comprise longitudinal edge means such that forcible introduction of said male insertion means into said cavity means releasibly joins the grasping means and the clamping means in tight compressive, rigid relation against inadvertent separation.

9. The skin clamping structure for releasibly holding skin away from a treatment site during medical therapy, said clamping structure comprising:
    radiation-transparent dermal grasping means comprising opposed surface means each of substantial area which contiguously engage skin and attachment means;
    clamping means comprising connecting means by which the clamping means are connected to the attachment means, bias means, bifurcated bias applying means by which the opposed surface means are caused to be biased toward each other and manual actuation means by which the bias applying means are selectively displaced counter to the bias to open the opposed surface means;
    the connection between the connection means and the attachment means being manually separable.

10. The skin clamping structure for releasibly holding skin away from a treatment site during medical therapy, said clamping structure comprising:
    radiation-transparent dermal grasping means comprising opposed surface means each of substantial area which contiguously engage skin and attachment means;
    clamping means comprising connection means by which the clamping means are connected to the attachment means, bias means, bifurcated bias applying means by which the opposed surface means are caused to be biased toward each other and manual actuation means by which the bias applying means are selectively displaced counter to the bias to open the opposed surface means;

said grasping means comprising two bodies of synthetic resinous foam.

11. The structure according to claim 10 wherein the synthetic resinous foam comprises high density styrofoam.

12. The skin clamping structure for releasibly holding skin away from a treatment site during medical therapy, said clamping structure comprising:

radiation-transparent dermal grasping means comprising opposed surface means each of substantial area which contiguously engage skin and attachment means;

clamping means comprising connection means by which the clamping means are connected to the attachment means, bias means, bifurcated bias applying means by which the opposed surface means are caused to be biased toward each other and manual actuation means by which the bias applying means are selectively displaced counter to the bias to open the opposed surface means;

the bias means comprising memory means sufficient to cause skin to be compressively held firmly against inadvertent removal but without material patient trauma between the opposed surface means.

13. Structure according to claim 12 wherein said memory means comprise spring means.

14. Structure according to claim 12 wherein said memory means comprise interrelated ratchet means and pawl means.

15. Structure according to claim 14 wherein said pawl means comprises releasible means.

16. Structure according to claim 12 wherein said memory means comprise latch means.

17. The skin clamping structure for releasibly holding skin away from a treatment site during medical therapy, said clamping structure comprising:

radiation-transparent dermal grasping means comprising opposed surface means each of substantial area which contiguously engage skin and attachment means;

clamping means comprising connection means by which the clamping means are connected to the attachment means, bias means, bifurcated bias applying means by which the opposed surface means are caused to be biased toward each other and manual actuation means by which the bias applying means are selectively displaced counter to the bias to open the opposed surface means;

the grasping means comprising opposed relatively large pads of unreinforced high density synthetic resinous foam.

18. A method of grasping loose skin and associated lymph systems and holding the same away from a radiation treatment area during treatment comprising the steps of:

manually holding a clamping mechanism in an open position counter to a bias;

gathering loose skin of a patient away from a treatment site into a position between large surface area radiologically transparent opposed clamping pads of the clamping mechanism;

manually releasing the clamping mechanism causing the bias to clamp the pads firmly though releasibly against the gathered skin disposed between the pads;

subjecting the treatment site to radiation therapy and thereafter manually removing the clamping mechanism from engagement with the skin.

19. A method according to claim 18 further comprising the step of removing the pads from the remainder of the removed clamping mechanism and discarding the pads.

20. A method according to claim 18 further comprising the step of removing the pads from the remainder of the removed clamping mechanism and discarding at least part of the clamping mechanism following the manual removing step.

21. A method of grasping loose skin and associated lymph systems from a radiation treatment area for a period comprising time involving medical therapy, comprising the following steps:

manually positioning a clamping mechanism in an open position;

gathering loose skin of a patient away from a treatment site into a position between large surface area radiologically transparent opposed synthetic resinous foam clamping pads of the clamping mechanism;

accommodating repositioning the clamping mechanism to displace the pads to clampingly close upon and hold the gathered skin therebetween against inadvertent separation;

subjecting the treatment site to radiation therapy against essentially taut skin and thereafter manually opening the clamped mechanism to remove the clamping mechanism from the skin.

22. Skin clamping structure for releasibly though essentially painlessly holding skin away from a treatment site during radiation therapy, the clamping structure comprising:

radiation transparent dermal grasping opposed synthetic resinous foam pads which selectively contiguously engage skin and by which the skin is held in a position other than from its normal location;

force applying means comprising means by which each pad is connected to the force applying means and means by which the pads are caused to compressively close upon, engage and hold the skin therebetween in said held position away from the treatment site during radiation therapy.

* * * * *